United States Patent [19]

Borror et al.

[11] 3,931,227

[45] Jan. 6, 1976

[54] 3,3-DI-(INDOLIN-5-YL)-PHTHALIDES AND NAPHTHALIDES

[75] Inventors: Alan L. Borror, Lexington; Paulina P. Garcia, Arlington, both of Mass.

[73] Assignee: Polaroid Corporation, Cambridge, Mass.

[22] Filed: Dec. 26, 1973

[21] Appl. No.: 427,580

Related U.S. Application Data

[63] Continuation-in-part of Ser. No. 241,807, April 6, 1972, abandoned.

[52] U.S. Cl.................................. 260/326.11 R
[51] Int. Cl.²............... C07D 209/08; C07D 209/18
[58] Field of Search ........................... 260/326.11 R

[56] References Cited
UNITED STATES PATENTS 3,509,174    4/1970    Lin ........................... 260/326.14 R

*Primary Examiner*—Lewis Gotts
*Assistant Examiner*—S. P. Williams
*Attorney, Agent, or Firm*—Sybil A. Campbell

[57] ABSTRACT

This invention relates to a new class of phthalein dyes useful as the color-forming material in either pressure sensitive or heat sensitive mark-forming systems. Such dyes comprise 3,3-disubstituted phthalides and 3,3-disubstituted naphthalides wherein the 3,3 substituents are indolin-5-yl radicals.

8 Claims, No Drawings

3,3-DI-(INDOLIN-5-YL)-PHTHALIDES AND NAPHTHALIDES

CROSS-REFERENCE TO RELATED PATENT APPLICATIONS

This application is a continuation-in-part of U.S. application Ser. No. 241,807 filed Apr. 6, 1972, now abandoned.

BACKGROUND OF THE INVENTION

1. Field of the Invention

The present invention relates to novel chemical compounds, and more specifically, it relates to a new class of phthalein dyes.

2. Background of the Invention

Various classes of phthalein dyes are known including phthaleins derived from heterocyclic compounds, such as, indoles and carbazoles and phthaleins derived from aminosubstituted and hydroxy-substituted carbocyclic aryl compounds, such as, anilines and notably phenols. Typically, these dyes possess spectral absorption characteristics alterable in response to changes in the pH of their environment and have found a number of different uses based upon their ability to change from one color to another, from colorless to colored and vice versa.

The present invention is concerned with a new class of phthalein dyes, namely, phthaleins including both phthalides and naphthalides derived from indolines.

SUMMARY OF THE INVENTION

It is, therefore, the primary object of the present invention to provide a novel class of phthalein dyes.

Other objects of this invention will in part be obvious and will in part appear hereinafter.

The invention accordingly comprises the products and compositions possessing the features, properties and the relation of elements which are exemplified in the following detailed disclosure, and the scope of the application of which will be indicated in the claims.

According to the present invention, there is provided a class of phthalein dyes comprising 3,3-disubstituted phthalides and 3,3-disubstituted naphthalides wherein the 3,3 substituents are indolin-5-yl radicals, the same or different. Though these dyes may be used as analytical reagents, for example, to measure changes in pH value, they possess certain properties that render them particularly useful as the chromogenic components in mark-forming systems.

For a fuller understanding of the nature of the invention, reference should be had to the following detailed description.

DESCRIPTION OF THE PREFERRED EMBODIMENTS

According to the present invention, it has been found that 5-indolinphthaleins normally appearing colorless or substantially colorless in solution or carrier are readily converted to their colored form when contacted with an electron-accepting material, for example, of the Lewis acid type and further, that they also are converted to their colored form upon application of heat. Because of these properties, the phthaleins of the present invention may be employed as the chromogenic or color-forming component in either pressure sensitive or heat sensitive mark-forming systems.

Typical of the indicator dyes of the present invention are those represented by the formula:

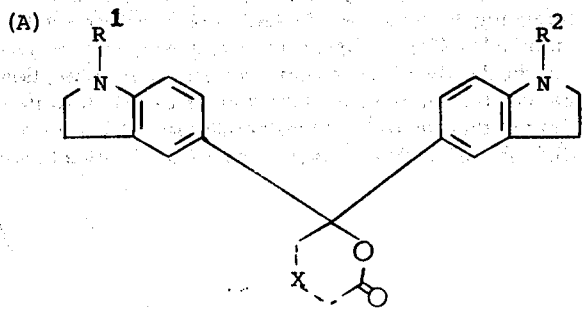

(A)

wherein $R^1$ and $R^2$ are selected from hydrogen, alkyl, cycloalkyl, aryl, aralkyl and alkaryl and X represents the atoms necessary to complete a ring-closing moiety selected from a phthalide and a naphthalide.

The groups $R^1$ and $R^2$, preferably unsubstituted, usually contain up to about 20 carbon atoms but may contain a grater number of carbon atoms as may be desired. When selected from alkyl, aralkyl and alkaryl, the alkyl group or the alkyl portion of the aralkyl and alkaryl groups may be branched or straight chain. Examples of groups that may comprise $R^1$ and $R^2$ include alkyl, such as methyl, ethyl, propyl, isopropyl, sec-butyl, tert-butyl, hexyl, octyl, decyl, dodecyl, hexadecyl, octadecyl and eicosanyl; cycloalkyl, such as cyclopentyl, cyclohexyl and cyclooctyl; aryl, such as phenyl and naphthyl; and aralkyl and alkaryl, such as, benzyl, phenethyl, phenylhexyl, p-hexylphenyl, p-octylphenyl, and p-dodecylphenyl.

In a preferred embodiment, the indicator dyes of the present invention are represented by the formula;

(B)

wherein R¹ and R², the same, are hydrogen or a group which is unsubstituted and which contains up to 20 carbon atoms selected from alkyl, cycloalkyl, aryl, alkaryl and particularly aralkyl and X represents the atoms necessary to complete a ring-closing moiety selected from phthalide, unsubstituted or substituted in the 7-position with COOR wherein R is hydrogen or alkyl having 1 to 4 carbon atoms and naphthalide, unsubstituted.

The dyes defined above and as represented in the foregoing formulas may contain substituents on the indolinyl radicals and/or on the ring-closing moiety as may be desired which do not interfere with the function of the dye for its selected ultimate use. Where it is desired that the dye be substantially immobile or non-diffusible in solution, it may be substituted with a bulky group, such as, a long chain substituent, e.g., dodecyloxy, hexadecyl or dodecylphenyl. Also it may be substituted with solubilizing groups, e.g., carboxy or sulfo to adjust the solubility in a given solution. Because of the convenience in the preparation, the dyes of the present invention preferably are symmetrical, i.e., bis phthalides and bis naphthalides wherein the two indolinyl radicals are the same, i.e., R¹ and R² are the same and the radicals contain the same substituents in the same position.

Typical substituents include branched or straight chain alkyl, such as, methyl, ethyl, isopropyl, n-butyl, t-butyl, hexyl, octyl, dodecyl, hexadecyl, octadecyl and eicosanyl; aryl, such as phenyl, 2-hydroxyphenyl, and naphthyl; alkaryl, such as, benzyl, phenethyl, phenylhexyl, p-octylphenyl, p-dodecylphenyl; alkoxy, such as, methoxy, ethoxy, butoxy, 1-ethoxy-2-(β-ethoxyethoxy), dodecyloxy and octadecyloxy; aryloxy, such as phenoxy, benzyloxy, naphthoxy; alkoxyalkyl, such as methoxyethyl, dodecyloxyethyl; halo such as, fluoro, bromo, and chloro; trifluoralkyl, such as, trifluoromethyl, mono- and bis- trifluoromethyl carbinol; sulfonamido; sulfamoyl; acyl and its derivatives; aminomethyl; amido; sulfonyl; sulfo; cyano; nitro; amino including mono- and disubstituted amino, e.g., N-ethyl amino and N,N'dimethylamino; carboxy; and hydroxyl.

Specific examples of dyes within the scope of the present invention are as follows:

(1) 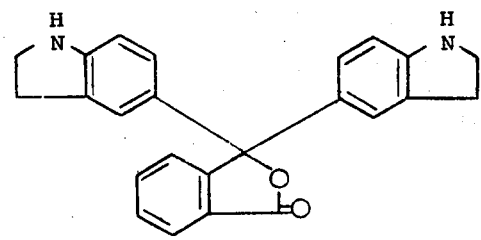

(2) 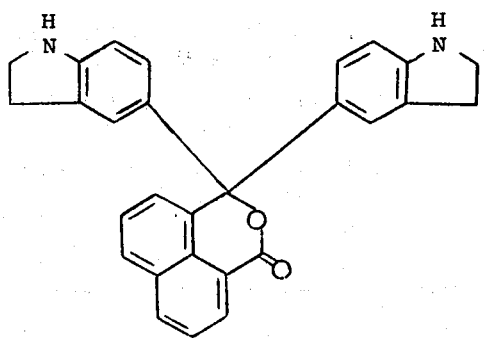

(3) 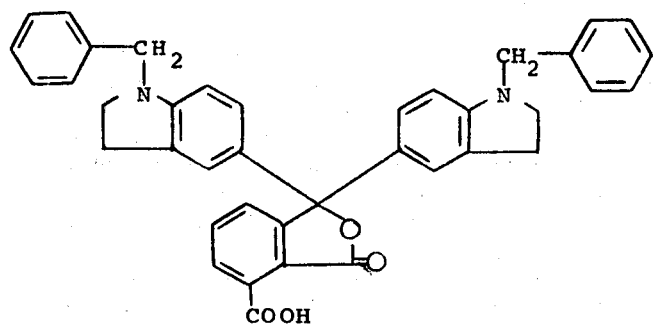

(4) 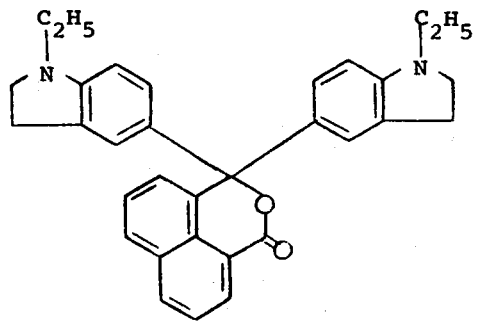

(5) 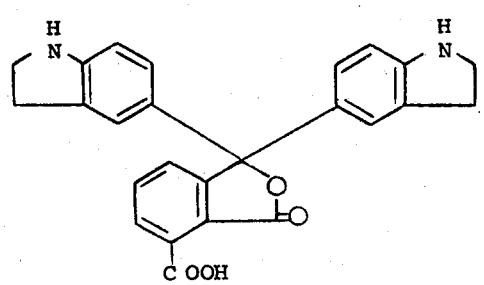

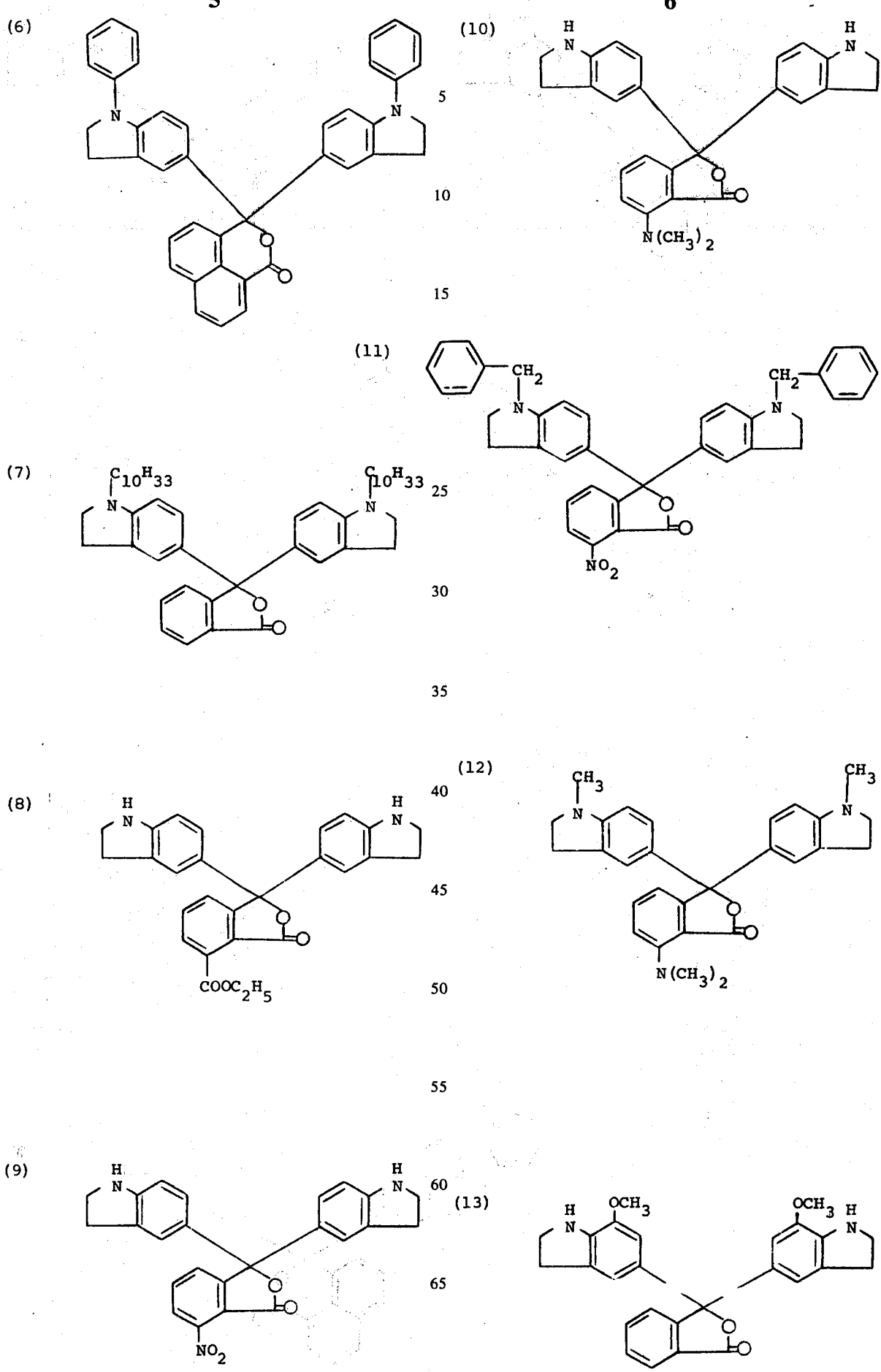

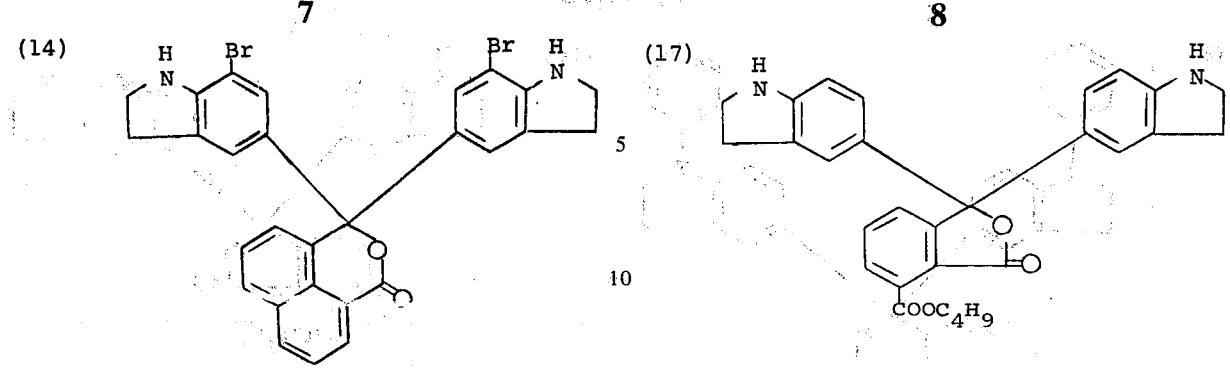
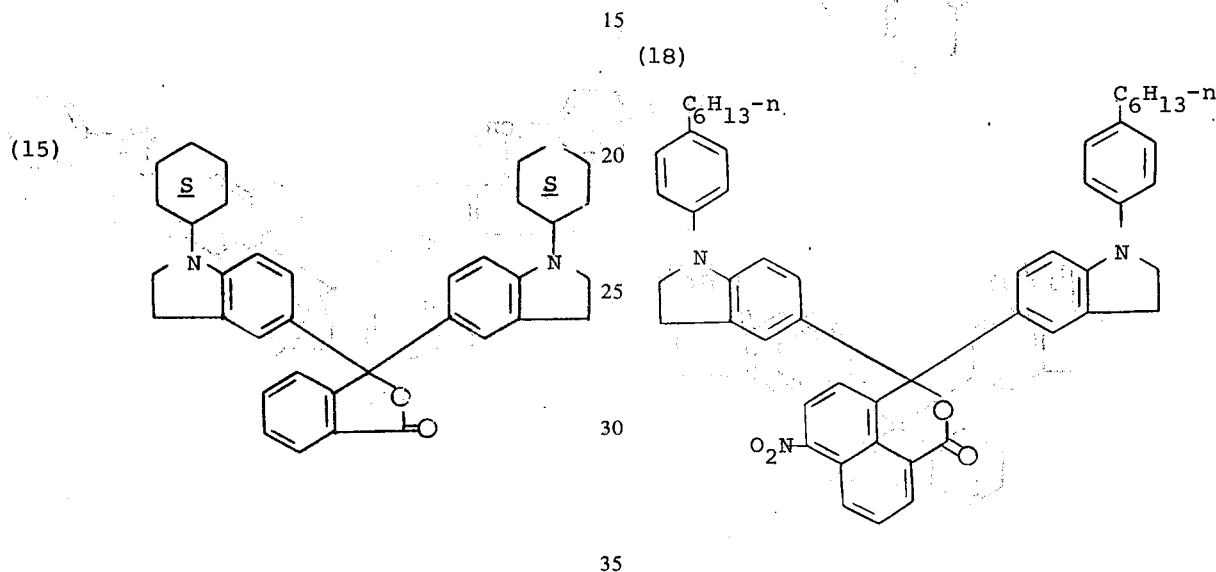
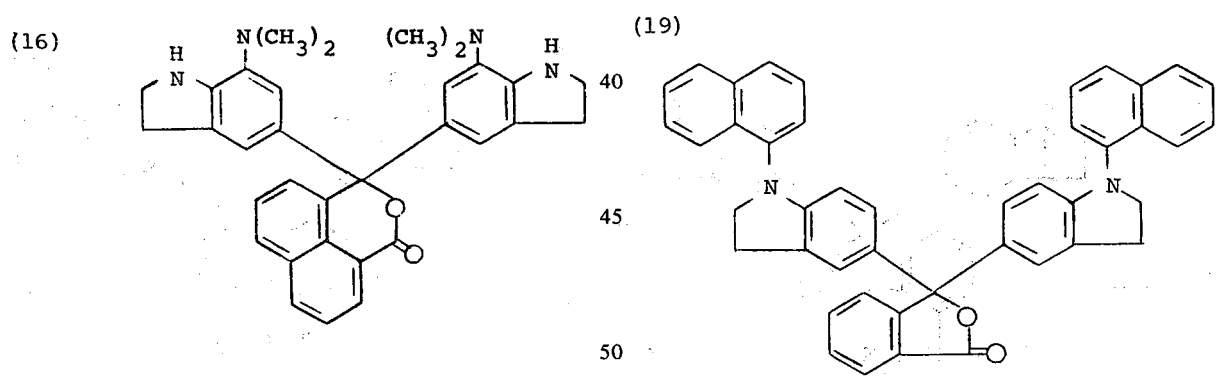
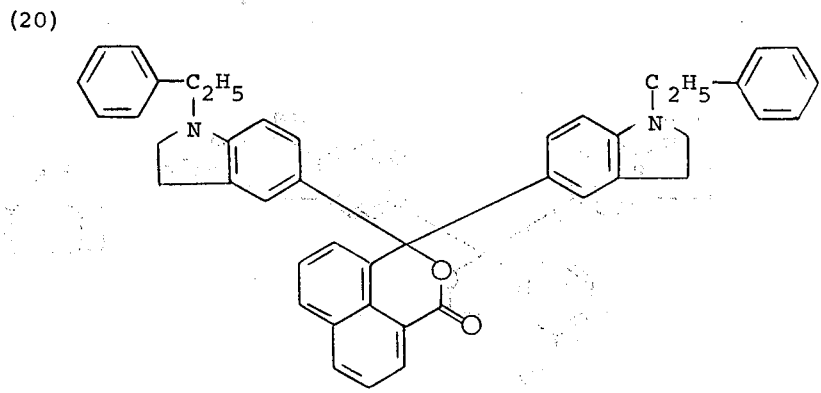

In synthesizing indolinphthaleins wherein the indoline is bonded to the phthalide or naphthalide through the 5-position, the indoline starting material should be substituted in the 1-position, i.e., the indoline should contain an appropriate blocking group substituted on the heterocyclic N atom in order to activate the 5-position for reaction with the phthalic or naphthalic acid reagent. Accordingly, the dyes of the present invention may be prepared by reacting an indoline substituted with alkyl, cycloalkyl, aryl, aralkyl or alkaryl on the heterocyclic N atom and a phthalic or naphthalic acid reagent at elevated temperatures in the presence of a suitable catalyst, such as, a Lewis acid catalyst as conventionally used in Friedel Craft reactions, e.g., aluminum chloride, ferric chloride, stannic chloride, boron trifluoride and zinc chloride. Also, an inert organic solvent capable of dissolving the reactants may be employed. Depending upon the dye product desired, the alkyl, cycloalkyl, aryl, aralkyl or alkaryl blocking groups substituted on the N atoms may be subsequently removed, e.g., by catalytic hydrogenation, to give corresponding indolinphthalein having hydrogen substituted on the heterocyclic N atoms.

The phthalic or naphthalic acid reagent selected to ultimately form the ring-closing moiety may be the acid, the acid chloride and preferably, the acid anhydride. The terms "phthalic acid reagent" and "naphthalic acid reagent" as used herein are intended to include the corresponding anhydrides and acid chlorides. These reagents may be substituted with groups, such as, carboxy, nitro and with other substituents as may be desired. Usually these groups are substituted in the 4- and preferably the 7-position of the phthalide ring-closing moiety and in the 6-position of the naphthalide ring-closing moiety. The carboxy and nitro groups may be converted to carbalkoxy and amino groups, respectively, in a known manner, for example, by reacting the carboxy-substituted phthalides and naphthalides with a lower alkyl alcohol to yield the corresponding carbalkoxy-substituted compound wherein the alkoxy portion of the carbalkoxy group contains 1 to 4 carbons. The starting indoline also may contain substituents other than the blocking group on the N atom provided that the carbon atom in the 5-position is available for reaction with the phthalic or naphthalic acid reagent. Typical substituents have been enumerated above.

The following Examples are given to further illustrate the present invention and are not intended to limit the scope thereof.

EXAMPLE 1

Preparation of the compound of formula (3):

To a well-stirred solution of 59.6 g. (0.5 mole) of indoline and 64.7 g. (0.5 mole) of ethyldiisopropylamine in 200 ml. chloroform was added 85.5 g. (0.5 mole) of benzyl bromide over a period of 45 minutes, after which it was refluxed for 8 hours. The reaction mixture was cooled to room temperature, washed with three 150 ml. portions of water (until washings were neutral to pH paper), and dried over anhydrous magnesium sulfate. The dried chloroform solution was distilled at reduced pressure and the residual liquid was distilled in vacuo to give 88 g. of N-benzylindoline, boiling range 127°–130°C/0.5 mm. A mixture of 38.4 g. (0.2 mole) of hemimellitic anhydride and 100 g. (0.72 mole) of freshly fused zinc chloride, previously ground in a mortar and pestle, was added to 83.6 g. (0.4 mole) of N-benzylindoline with vigorous stirring at 100°C. in an atmosphere of nitrogen. The temperature of the reaction mixture was raised to 115°–120°C. and kept at this temperature for 5 hours. The green-blue solid mass was cooled to room temperature, pulverized and then triturated with 30% acetic acid until it was free from zinc ions. The light green solid was washed thoroughly with water and dried over sodium hydroxide in vacuo at 50°C. The dried powder was extracted with hot chloroform. The combined chloroform extracts were concentrated to 200 ml. and poured slowly into 1.5 liters of hexane with vigorous stirring. The light green solid was removed by suction filtration and dried in vacuo at 50°C. This solid was extracted in a Soxhlet with 1 liter of benzene for 24 hours. The benzene extract was concentrated to about one-half its original volume and poured into 1.5 liters of hexane. The pale green precipitate was removed by suction filtration and dried in vacuo at 50°C. to give 48.2 g. (41% by weight) of the title compound (melting range 147°–149°C.).

EXAMPLE 2

Preparation of the compound of formula (5):

A suspension of 5.93 g. (10.0 mm.) of the compound prepared in Example 1 in 250 ml. of ethanol-water (1:1) containing 1 ml. of hydrochloric acid (sp. gr. 1.19) and 2.0 g. of 10% palladium-on-carbon was allowed to absorb hydrogen in a Parr shaker until the theoretical uptake had been reached. The catalyst was removed by filtration through Celite and then washed thoroughly with boiling ethanol. The combined filtrate and washings were evaporated to dryness in a flash evaporator. The residue was dried in vacuo at 60°C. over sodium hydroxide. There was obtained 4.0 g. of the title compound (melting range 190°–195°C.).

EXAMPLE 3

Preparation of the compound of formula (8):

A solution of 3.0 g. of the compound prepared in Example 2 in 50 ml. of absolute ethanol saturated with dry hydrogen chloride at 15°–20°C. was refluxed overnight. The ethanol was removed on a flash evaporator, and the residue was treated with 120 ml. of 5% sodium bicarbonate. The purple solid was removed by suction filtration, washed thoroughly with water, and dried in vacuo over Drierite at 50°C. to give 3.3 g. of the title compound (melting range 100°–105°C.).

It was observed that the phthalein compounds prepared in the above Examples immediately assumed color when contacted with glacial acetic acid. Also, it was observed that these compounds, when adsorbed on a silica matrix, were converted to their colored form upon applying heat.

Phthalic anhydride and naphthalic anhydride may be used instead of hemimellitic anhydride to yield the corresponding 5-indoline phthalides and naphthalides. For example, naphthalic anhydride may be substituted for hemimellitic anhydride in Example 1 above to yield N-benzylindoline-5-yl naphthalide, and this compound may be treated with palladium-on-carbon, as in Example 2, to yield indolin-5-yl naphthalide.

As noted previously, such properties render the subject phthalein compounds useful as the color-forming material in mark-forming systems employing pressure sensitive or heat sensitive copying papers, such as, the mark-forming systems described in U.S. Pat. Nos. 3,491,111 and 2,967,785, respectively. As used in pressure sensitive systems, marking in desired areas on support webs or sheets may be accomplished by effecting localized reactive contact between the color-forming material and an electron-accepting material of the Lewis acid type, such as, phenolic polymers and acid clays, to form a dark or contrasting color in the intended image-marking areas. As used in heat sensitive systems, marking in desired areas of a heat sensitive sheet containing the color-forming material may be accomplished by placing a graphic original in heatconductive contact with the heat sensitive sheet and irradiating the composite to develop a differential heat pattern at the printed surface of the original. The heat pattern formed upon irradiation generates color in the color-forming material to form a reproduction of the printed matter in the heat sensitive sheet. Such mark-forming systems employing pressure or heat for reproducing a graphic original are well known in the art.

Since certain changes may be made in the above product and composition without departing from the scope of the invention herein involved, it is intended that all matter contrained in the above description shall be interpreted as illustrative and not in a limiting sense.

What is claimed is:

1. A compound of the formula:

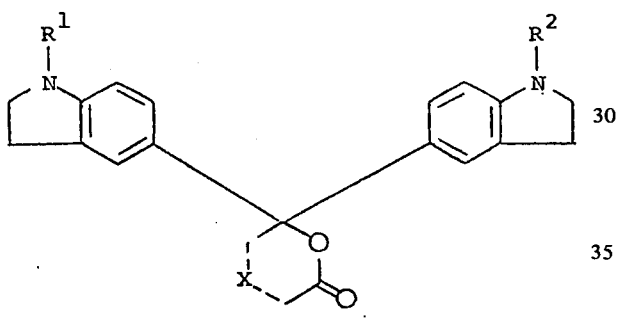

wherein $R^1$ and $R^2$, the same, are hydrogen or a group which is unsubstituted and which contains up to 20 carbon atoms selected from alkyl; cycloalkyl; aryl selected from phenyl and naphthyl; alkaryl wherein the aryl portion of said alkaryl is phenyl; and aralkyl wherein the aryl portion of said aralkyl is phenyl; and X represents the atoms necessary to complete a ring-closing moiety selected from phthalide, unsubstituted or substituted in the 7-position with —COOR wherein R is hydrogen or alkyl containing 1 to 4 carbon atoms and naphthalide, unsubstituted.

2. A compound as defined in claim 1 wherein $R^1$ and $R^2$ are aralkyl.

3. A compound as defined in claim 2 wherein $R^1$ and $R^2$ are benzyl.

4. A compound as defined in claim 1 wherein $R^1$ and $R^2$ are hydrogen.

5. A compound as defined in claim 1 wherein X represents phthalide.

6. 3,3-di-(indolin-5-yl)-7-carboxyphthalide.

7. 3,3-di-(indolin-5-yl)-7-carbethoxyphthalide.

8. 3,3-di-(N-benzylindolin-5-yl)-7-carboxyphthalide.

* * * * *